(12) United States Patent
Schad et al.

(10) Patent No.: US 11,918,024 B2
(45) Date of Patent: Mar. 5, 2024

(54) COATING COMPOSITION AND METHOD OF MAKING AND USING THE SAME

(71) Applicant: SENSIENT COLORS LLC, St. Louis, MO (US)

(72) Inventors: Beverly A. Schad, Union, MO (US); Houston Smith, St. Louis, MO (US)

(73) Assignee: Sensient Colors LLC, St. Louis, MO (US)

( * ) Notice: Subject to any disclaimer, the term of this patent is extended or adjusted under 35 U.S.C. 154(b) by 220 days.

(21) Appl. No.: 16/500,641

(22) PCT Filed: Apr. 3, 2018

(86) PCT No.: PCT/US2018/025863
§ 371 (c)(1),
(2) Date: Oct. 3, 2019

(87) PCT Pub. No.: WO2018/187314
PCT Pub. Date: Oct. 11, 2018

(65) Prior Publication Data
US 2020/0107570 A1   Apr. 9, 2020

Related U.S. Application Data

(60) Provisional application No. 62/480,966, filed on Apr. 3, 2017.

(51) Int. Cl.
| | | |
|---|---|---|
| *A23P 20/10* | (2016.01) | |
| *A23G 3/34* | (2006.01) | |
| *A61K 9/00* | (2006.01) | |
| *A61K 47/10* | (2017.01) | |
| *A61K 47/26* | (2006.01) | |
| *A61K 47/42* | (2017.01) | |
| *A61K 47/44* | (2017.01) | |

(52) U.S. Cl.
CPC .............. *A23P 20/11* (2016.08); *A23G 3/343* (2013.01); *A61K 9/0056* (2013.01); *A61K 47/10* (2013.01); *A61K 47/26* (2013.01); *A61K 47/42* (2013.01); *A61K 47/44* (2013.01)

(58) Field of Classification Search
None
See application file for complete search history.

(56) References Cited

U.S. PATENT DOCUMENTS

| 5,919,574 A | 7/1999 | Hoagland |
| 10,307,397 B2 * | 6/2019 | Allen ...................... A61K 31/05 |
| 2015/0305382 A1 | 10/2015 | Jelavich et al. |
| 2016/0353765 A1 * | 12/2016 | Bogdan-Smigielska ..................... A23G 4/025 |

FOREIGN PATENT DOCUMENTS

| JP | 2001190575 A | 7/2001 | |
| JP | 5992247 B2 * | 9/2016 | ......... A61K 31/7088 |

OTHER PUBLICATIONS

International Search Report and Written Opinion, International Application No. PCT/US2018/025863, dated May 28, 2018, 7 pages.

* cited by examiner

*Primary Examiner* — Lakshmi S Channavajjala
(74) *Attorney, Agent, or Firm* — GTC Law Group PC & Affiliates

(57) ABSTRACT

The present disclosure provides a coating composition including a pectin and a non-glycerol sugar alcohol. The pectin can be present in an amount by weight of at least 30.0% and at most 50.0%. The non-glycerol sugar alcohol can be present in an amount by weight of at least 10.0%) and at most 40.0%. The pectin can be present in a ratio of at least 1:1 and at most 5:1 relative to the non-glyercol sugar alcohol. The present disclosure also provides coating suspensions, coatings, and coated substrates related to the coating composition. The present disclosure also provides methods of making and using the coating compositions.

19 Claims, No Drawings

COATING COMPOSITION AND METHOD OF MAKING AND USING THE SAME

CROSS-REFERENCE TO RELATED APPLICATIONS

This application is a national stage entry of International Application No. PCT/US2018/025863, filed Apr. 3, 2018, and claims priority to U.S. Provisional Patent Application No. 62/480,966, filed Apr. 3, 2017, both of which are incorporated herein by reference in their entirety.

BACKGROUND

Gummy dosage forms are increasingly prevalent in pharmaceutical and nutraceutical dosing. Storage stability remains a problem for gummy dosage forms. Accordingly, a need exists for improving gummy dosage form stability.

Food coating is also in need of improved coating compositions, particularly relating to the provision of color and flavor.

BRIEF SUMMARY

In an aspect, the present disclosure provides a coating composition. The coating composition can include a pectin and a non-glycerol sugar alcohol. The pectin can be present in an amount by weight of at least 30.0% and at most 50.0%. The non-glycerol sugar alcohol can be present in an amount by weight of at least 10.0% and at most 40.0%. The pectin can be present in a ratio of at least 1:1 and at most 5:1 relative to the non-glyercol sugar alcohol.

In another aspect, the present disclosure provides a coating suspension. The coating suspension includes the coating composition as described herein and a solvent.

In a further aspect, the present disclosure provides a method of using a coating suspension. The method includes applying the coating suspension to a substrate.

In yet another aspect, the present disclosure provides a method of making the coating composition described herein. The method includes combining ingredients of the coating composition.

In yet a further aspect, the present disclosure provides a coating. The coating includes the non-volatile ingredients of the coating composition and/or suspension described herein.

In an additional aspect, the present disclosure provides a coated substrate. The coated substrate include a substrate and the coating described herein.

DETAILED DESCRIPTION

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising", "including", or "having" should be interpreted as referring to elements, components, or steps in a non-exclusive manner, so the referenced elements, components, or steps may be combined with other elements, components, or steps that are not expressly referenced. Embodiments referenced as "comprising", "including", or "having" certain elements are also contemplated as "consisting essentially of" and "consisting of" those elements, unless the context clearly dictates otherwise. It should be appreciated that aspects of the disclosure that are described with respect to a system are applicable to the methods, and vice versa, unless the context explicitly dictates otherwise.

Numeric ranges disclosed herein are inclusive of their endpoints. For example, a numeric range of between 1 and 10 includes the values 1 and 10. When a series of numeric ranges are disclosed for a given value, the present disclosure expressly contemplates ranges including all combinations of the upper and lower bounds of those ranges. For example, a numeric range of between 1 and 10 or between 2 and 9 is intended to include the numeric ranges of between 1 and 9 and between 2 and 10.

The present disclosure provides a coating composition. The coating composition comprises pectin and a non-glycerol sugar alcohol.

The pectin can have a molecular weight of at least 60 kg/mol, at least 65 kg/mol, at least 70 kg/mol, at least 75 kg/mol, at least 80 kg/mol, at least 85 kg/mol, at least 90 kg/mol, at least 95 kg/mol, or at least 100 kg/mol. The pectin can have a degree of methyl esterification of greater than 50. Suitable pectin can be purchased from CP Kelco, Atlanta, GA.

The pectin can be present in the coating composition in an amount by weight of at least 30.0%, at least 31.0%, at least 32.0%, at least 33.0%, at least 34.0%, at least 35.0%, at least 36.0%, at least 37.0%, at least 37.5%, at least 38.0%, at least 39.0%, or at least 39.5%. The pectin can be present in the coating composition in an amount by weight of at most 50.0%, at most 49.0%, at most 48.0%, at most 47.0%, at most 46.0%, at most 45.0%, at most 44.0%, at most 43.0%, at most 42.5%, at most 42.0%, at most 41.0%, or at most 40.5%.

The non-glycerol sugar alcohol can be selected from the group consisting of sorbitol, mannitol, xylitol, isomalt, hydrogenated starch hydrolysates, and combinations thereof. The non-glycerol sugar alcohol can be sorbitol. The non-glycerol sugar alcohol can be non-GMO non-glycerol sugar alcohol. The sorbitol can be non-GMO sorbitol.

The non-glycerol sugar alcohol can be present in the coating composition in an amount by weight of at least 10.0%, at least 11.0%, at least 12.0%, at least 13.0%, at least 14.0%, at least 15.0%, at least 16.0%, at least 17.0%, at least 17.5%, at least 18.0%, at least 18.5%, at least 19.0%, at least 19.5%, or at least 20.0%. The non-glycerol sugar alcohol can be present in the coating composition in an amount by weight of at most 40.0%, at most 39.0%, at most 37.5%, at most 35.0%, at most 32.5%, at most 30.0%, at most 29.0%, at most 28.0%, at most 27.0%, at most 26.0%, at most 25.0%, at most 24.5%, at most 24.0%, at most 23.5%, at most 23.0%, at most 22.5%, at most 22.0%, at most 21.5%, at most 21.0%, at most 20.5%, or at most 20.0%.

The coating composition can optionally include a plasticizer, such as glycerin. It should be appreciated that glycerin can perform some of the function of the non-glycerol sugar alcohol, but is identified as a separate ingredient here for the additional properties that result from its inclusion. The plasticizer can be present in an amount by weight of at least 0.01%, at least 0.1%, at least 0.5%, at least 1.0%, at least 2.0%, at least 2.5%, at least 3.0%, at least 4.0%, or at least 5.0%. The plasticizer can be present in an amount by weight of at most 10.0%, at most 9.0%, at most 8.0%, at most 7.5%, at most 7.0%, at most 6.0%, or at most 5.0%.

The coating composition can optionally include an oil-based plasticizer. The oil-based plasticizer can be present in the coating composition in an amount by weight of at least 0.01%, at least 0.1%, at least 0.5%, at least 1.0%, at least 2.0%, at least 3.0%, at least 4.0%, at least 5.0%, at least 6.0%, at least 7.0%, or at least 8.0%. The oil-based plasticizer can be present in an amount by weight of at most 15.0%, at most 14.0%, at most 13.0%, at most 12.5%, at most 12.0%, at most 11.5%, at most 11.0%, at most 10.5%, at most 10.0%, at most 9.5%, at most 9.0%, at most 8.5%, or at most 8.0%.

The oil-based plasticizer can be selected from the group consisting of acetylated monoglycerides, medium chain triglycerides (MCT), propylene glycol dicaprylate/dicaprate (for example, Miglyol® 840, available commercially from Peter Cremer North America, Cincinnati, OH), oil based plasticizers contained within oil soluble flavor incorporations, fatty acid based plasticizers, and combinations thereof. In certain aspects, the oil-based plasticizer is acetylated monoglycerides or fatty acid based plasticizers.

The coating composition can include a film forming agent. The film forming agent can be present in the coating composition in an amount by weight of at least 0.01%, at least 0.1%, at least 0.5%, at least 1.0%, at least 2.0%, at least 3.0%, at least 4.0%, at least 5.0%, at least 6.0%, at least 7.0%, or at least 8.0%. The film forming agent can be present in an amount by weight of at most 15.0%, at most 14.0%, at most 13.0%, at most 12.5%, at most 12.0%, at most 11.5%, at most 11.0%, at most 10.5%, at most 10.0%, at most 9.5%, at most 9.0%, at most 8.5%, or at most 8.0%.

The film forming agent (which functions as a binder and could also be referred to herein as a binder) can be hydroxypropyl cellulose (HPC), hydroxypropyl methyl cellulose (HPMC), or a combination thereof. In some cases, the HPC and/or HPMC can be low molecular weight HPC and/or HMPC. In some cases, the film forming agent has a viscosity of between 2.0 and 6.0 cP. In some cases, the HPC has a viscosity of 2.0 cP to 5.9 cP, including 2.0 cP to 2.9 cP and 3.0 cP to 5.9 cP. In some cases, the HPMC is HPMC 3 cp.

The coating composition can include a wax. The wax can be present in the coating composition in an amount by weight of at least 0.01%, at least 0.1%, at least 0.5%, at least 1.0%, at least 2.0%, at least 3.0%, at least 4.0%. The wax can be present in the coating composition in an amount by weight of at most 5.0%, at most 4.5%, at most 4.0%, at most 3.5%, at most 3.0%, or at most 2.5%. In some cases, the amount of wax present can be within 5%, 10%, 15%, 20%, or 25% of an oil content of the coating composition, which allows formation of a waxy emulsion during the stirring, which can create slip for the substrate during application.

The wax can be selected from the group consisting of carnauba wax, beeswax, vegetable-based waxes, and combinations thereof. The wax can be carnauba wax.

The coating composition can optionally include an opacifying agent. The opacifying agent can be present in the coating composition in an amount by weight of at least 10.0%, at least 10.5%, at least 11.0%, at least 11.5%, at least 12.0%, at least 12.5%, at least 13.0%, at least 13.5%, at least 14.0%, at least 14.5%, or at least 15.0%. The opacifying agent can be present in the coating composition in an amount by weight of at most 20.0%, at most 19.5%, at most 19.0%, at most 18.5%, at most 18.0%, at most 17.5%, at most 17.0%, at most 16.5%, at most 16.0%, at most 15.5%, or at most 15.0%.

The opacifying agent can be selected from the group consisting of titanium dioxide, calcium carbonate, Sensient® Avalanche™ (available commercially from Sensient Colors LLC, St. Louis, MO), microcrystalline cellulose, other ingredients rendering opacification, and combinations thereof.

The coating composition can optionally include a non-sugar-alcohol sweetening agent. The non-sugar-alcohol sweetening agent can be present in the coating composition in an amount by weight of at least 0.01%, at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. The non-sugar-alcohol sweetening agent can be present in the coating composition in an amount by weight of at most 10.0%, at most 9.5%, at most 9.0%, at most 8.5%, at most 8.0%, at most 7.5%, at most 7.0%, at most 6.0%, at most 5.0%, at most 4.0%, at most 3.0%, or at most 2.5%.

The non-sugar-alcohol sweetening agent can be selected from the group consisting of an artificial sweetener, a natural sweetener, such as erythritol, stevia, a sugar, and combinations thereof.

The natural sweetener can be present in the coating composition in an amount by weight of at least 0.01%, at least 0.1%, at least 0.5%, at least 1.0%, or at least 1.5%. The natural sweetener can be present in the coating composition in an amount by weight of at most 2.0%, at most 1.5%, at most 1.0%, or at most 0.5%.

The artificial sweetener can be selected from the group consisting of sucralose, acesulfame, aspartame, and combinations thereof. The artificial sweetener can be present in the coating composition in an amount by weight of at least 0.01%, at least 0.1%, at least 0.5%, at least 1.0%, or at least 1.5%. The artificial sweetener can be present in the coating composition in an amount by weight of at most 2.0%, at most 1.5%, at most 1.0%, or at most 0.5%.

The sugar can be selected from the group consisting of sucrose, fructose, and combinations thereof.

The coating composition can include an adjuvant. An adjuvant, as used herein, refers to an additive that has some complementary benefit to an existing benefit of the substrate that is being coated. Examples of suitable adjuvants include, but are not limited to, vitamins, such as vitamin C (ascorbic acid), vitamin D2 (ergocalciferol), vitamin D3 (cholecalciferol), vitamin K1 (phylloquinone), and vitamin K2 (menaquinone, menatetrenone); thiamin; riboflavin; niacin; nicotinic acid; pantothenic acid; pyridoxine; biotin; folic acid; folate; cyanobalamin; methycobalamin; and the like. Using vitamin C as a specific non-limiting example, vitamin C can be applied within a powder coat (see below) to help support the immunie system. Applying vitamin C to the outside of a substrate, such as a gummy, can aid in maintaining the shelf life of the vitamin C and also produce color integrity. In many cases, vitamin C can oxidize, thus turning the orange color to a brownish color. Using vitamin C as an adjuvant in the powder base can reduce this effect.

The coating composition can include a flavorant or sensate. The flavorant can be a spray dried flavorant, a dried crystal flavorant, a granule flavorant, a liquid flavorant, or a combination thereof. The spray dried flavorant, the dried crystal flavorant, the granule flavorant, the liquid flavorant, or the combination thereof can comprise a synthetic flavoring agent, an artificial flavoring agent, a natural flavoring agent, or a combination thereof. The spray dried flavorant, the dried crystal flavorant, the granule flavorant, the liquid flavorant, or the combination thereof can provide a flavor selected from the group consisting of almond, amaretto, apple, green apple, apple-cherry-berry, apple-honey, apricot, bacon, banana, barbeque, beef, roast beef, beef steak, berry, berry blue, birch beer, spruce beer, blackberry, bloody mary, blueberry, boysenberry, brandy, bubble gum, butter, butter pecan, buttermilk, butterscotch, candy corn, cantaloupe, cantaloupe lime, caramel, carrot, cassia, caviar, celery, cereal, champagne, cherry, cherry cola, cherry maraschino, wild cherry, black cherry, red cherry, cherry-cola, chicken, chocolate, chocolate almond, cinnamon spice, citrus, citrus blend, citrus-strawberry, clam, cocoa, coconut, toasted coconut, coffee, coffee almond, cola, cola-vanilla, cookies & cream, cotton candy, cranberry, cranberry-raspberry, cream, cream soda, dairy type cream, creme de menthe, cucumber, black currant, dulce de leche, egg nog, pork fat, non-pork fat, anchovy fish, herring fish, sardine fish, frankfurter, fried garlic, sauteed garlic, gin, ginger ale, ginger beer, graham cracker type, grape, grape grapefruit, grapefruit-lemon, grapefruit-lime, grenadine, grill, guarana, guava, hazelnut, honey, roasted honey, ice cream cone, jalapeno, key lime, kiwi, kiwi-banana, kiwi-lemon-lime, kiwi-strawberry, kola champagne, lard type, lemon, lemon custard, lemonade, pink lemonade, lemon-lime, lime, malt, malted milk, mango, mango-pineapple, maple, margarita, marshmallow, meat type, condensed milk, cooked milk, mint, mirepoix, mocha, mochacinna, molasses, mushroom, sauteed mushroom, muskmelon, nectarine, neopolitan, green onion, sauteed onion, orange, orange cordial, orange creamsicle, orange creme, orange peach mango, orange strawberry banana, creamy orange, mandarin orange, orange-passionguava, orange-pineapple, papaya, passion fruit, peach, peach-mango, peanut, roasted peanut, pear, pecan danish, pecan praline, pepper, peppermint, pimento, pina colada, pina colada/pineapple-coconut, pineapple, pineapple-orange, pistachio, pizza, pomegranate, baked potato, prune, punch, citrus punch, tropical punch, cherry fruit punch, grape punch, raspberry, black raspberry, blue raspberry, red raspberry, raspberry-blackberry, raspberry-ginger ale, raspberry-lime, root beer, rum, sangria, sarsaparilla, sassafras, sausage, sausage pizza, seafood, shrimp, hickory smoke, mesquite smoke, sour, sour cream, sour cream and onion, spearmint, strawberry, strawberry margarita, jam type strawberry, strawberry-kiwi, burnt sugar, tallow, tamarind, tangerine-lime, tangerine, tea, tequila, toffee, triple sec, tropical fruit mix, turkey, tutti frutti, vanilla, vanilla cream, vanilla custard, french vanilla, vegetable, vermouth, vinegar, balsamic vinegar, watermelon, whiskey, wildberry, wine, yogurt, and combinations thereof. The flavors described herein can be use alone or in combination with sensates described herein for experiential sensations of cooling, heating and tingling effects, such as use in combination with Sensient® Smoothenol® products.

The spray dried flavorant, the dried crystal flavorant, the granule flavorant, or a combination thereof can be present in the coating composition in an amount by weight of at least 0.1 at least 1.0% at least 2% at least 3.0%, at least 4.0%, at least 5.0%, at least 6.0%, at least 7.0%, at least 8.0%, at least 9.0%, at least 10.0%, at least 11.0%, at least 12.0%, or at least 12.5%. The spray dried flavorant, the dried crystal flavorant, the granule flavorant, or a combination thereof can be present in the coating composition in an amount by weight of at most 15.0%, at most 14.0%, at most 13.0%, at most 12.0%, at most 11.0%, at most 10.0%, at most 9.0%, at most 8.0%, at most 7.0%, at most 6.0%, or at most 5.0%.

The liquid flavorant can be present in the coating composition in an amount by weight of at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. The liquid flavorant can be present in the coating composition in an amount by weight of at most 9.0%, at most 8.0%, at most 7.0%, at most 6.0%, at most 5.0%, at most 4.0%, at most 3.0%, at most 2.0%, or at most 1.0%.

The coating composition can include a sensate. The sensate can be a spray dried sensate, a dried crystal sensate, a granule sensate, a liquid sensate, or a combination thereof. The spray dried sensate, the dried crystal sensate, the granule sensate, the liquid sensate, or a combination thereof can provide a hot sensation, a cool sensation, a tingling sensation, or a combination thereof. In some cases, the sensate can be combined with a flavorant to provide a combination flavorant and sensate that combined the flavors and the sensations disclosed herein. In the event that a flavorant is combined with a sensate, the combination flavorant and sensate should be present in an amount that is equal to the amounts described herein with respect to flavorants and sensates.

The spray dried sensate, the dried crystal sensate, the granule sensate, or a combination thereof can be present in the coating composition in an amount by weight of at least 1% at least 2% at least 3.0%, at least 4.0%, at least 5.0%, at least 6.0%, at least 7.0%, at least 8.0%, at least 9.0%, at least 10.0%, at least 11.0%, at least 12.0%, or at least 12.5%. The spray dried sensate, the dried crystal sensate, the granule sensate, or a combination thereof can be present in the coating composition in an amount by weight of at most 15.0%, at most 14.0%, at most 13.0%, at most 12.0%, at most 11.0%, at most 10.0%, at most 9.0%, at most 8.0%, at most 7.0%, at most 6.0%, or at most 5.0%.

The liquid sensate can be present in the coating composition in an amount by weight of at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. The liquid sensate can be present in the coating composition in an amount by weight of at most 9.0%, at most 8.0%, at most 7.0%, at most 6.0%, at most 5.0%, at most 4.0%, at most 3.0%, at most 2.0%, or at most 1.0%.

The coating composition can include a flavor masking agent. The flavor masking agent can be selected from the group consisting of Smoothenol®, Smoothenol 2G® or numerical G smoothenol; such as 3G, 4G and in the forms of BitterFix™, AstringentFix™, FunctionalFix™, BurnFix™, SourFix™ (all available commercially from Sensient Flavors LLC, Hoffman Estates, IL), and combinations thereof. The flavor masking agent can be present in an amount by weight of at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. The flavor masking gent can be present in an amount by weight of at most 9.0%, at most 8.0%, at most 7.0%, at most 6.0%, at most 5.0%, at most 4.0%, at most 3.0%, at most 2.0%, or at most 1.0%. In some cases, the flavor masking agent can be combined with a flavorant, a sweetener, a sweetener enhancer, or the like. In some cases, the flavor masking agent can be contained in a combination product, such as Mafco's Magnasweet® line of products (available commercially from MAFCO Worldwide LLC, Camden, NJ).

The coating composition can include a colorant. The colorant can be selected from the group consisting of a pigment, a dye, an exempt colorant (i.e., a colorant from a natural source or (certified) organic based), and combinations thereof. The colorant can be present in an amount by weight of at least 0.01% at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. The colorant can be present in an amount by weight of at most 20.0%, at most 17.5%, at most 15.0%, at most 12.5%, or at most 10.0%.

In certain cases, the colorant can be supplied in the form of a colorant liquid and/or emulsion. In these cases, the colorant in the form of a liquid and/or emulsion can be added directly to the coating suspension described elsewhere herein. In those cases, the amount of colorant can be determined based on the percentages above and isolating the weight contribution of the colorant in the liquid and/or emulsion. When added directly to the coating suspension, the colorant in the form of a liquid and/or emulsion can be present in the suspension in an amount by weight of at least 0.01% at least 0.1%, at least 0.5%, at least 1.0%, at least 2.0%, at least 2.5%, at least 3.0%, at least 3.5%, at least 4.0%, at least 4.5%, at least 5.0%, at least 6.0%, at least 7.0%, or at least 8.0%. When added directly to the coating suspension, the colorant in the form of a liquid and/or emulsion can be present in an amount by weight of at most 20.0%, at most 17.5%, at most 15.0%, at most 14.0%, at most 13.0%, at most 12.5%, at most 12.0%, at most 11.0%, or at most 10.0%.

The coating composition can include an acidifying agent. The acidifying agent can be selected from the group consisting of citric acid, malic acid, ascorbic acid, and combinations thereof. The acidifying agent can be present in the coating composition in an amount by weight of at least 0.01%, at least 0.1%, at least 0.25%, or at least 0.5%. The acidifying agent can be present in the coating composition in an amount by weight of at most 1.0%, at most 0.9%, at most 0.75%, or at most 0.5%.

The coating composition can be substantially free of various components that are commonly used with pectin. The coating composition can be substantially free of divalent cations, such as calcium or magnesium, and in particular calcium.

The coating composition can be substantially free of genetically modified organisms or products thereof.

The present disclosure provides a powder base. The powder base can be applied to a substrate prior to the application of the coating composition and/or coating suspension. The power base can be added to the substrate, and is particularly useful when added to sticky substrates, at a weight gain of at least 0.5%, at least 1.0%, at least 1.5%, at least 2.0%, at least 2.5%, or at least 3.0%. Application of the powder base can be followed by subsequent coating by the coating composition and/or coating suspension. The powder base can include a polymer, such as maltodextrin, tapioca dextrin, high-amylose or other cellulosic materials, and the like. The powder base can include extra flavor, adjuvants, sweeteners, opacifying agents, probiotics, masking agents, and the like. These components can be present in amounts described elsewhere herein in the context of the coating composition or in amounts understood to be beneficial by those having ordinary skill in the art.

The use of the powder base can be determined by following a line of decision making either described in this paragraph or understood by those having ordinary skill in the art. As one example of this decision making, a two-step decision process can involve the following: Step 1—Will the coating composition/suspension be used to achieve a non-slip surface? If yes, then coat with the coating composition/suspension. If no, then proceed to step 2. Step 2—Use the powder base to add additional ingredients to the surface of the substrate (e.g., gummy), such as adjuvants, probiotics/ prebiotics, additional flavorants, taste masking agents, colorants, or other excipients. Apply powder base and then top coat with the coating composition/suspension.

The present disclosure provides a coating suspension. The coating suspension can include the coating composition, as described elsewhere herein, and a solvent. The solvent can be selected from the group consisting of water, alcohol, such as methanol, ethanol, isopropanol, butyl alcohol, and combinations thereof.

The coating suspension can have a solids content of at least 6.0%, at least 6.5%, at least 7.0%, at least 7.5%, 8.0%, at least 8.5%, at least 9.0%, at least 9.5%, at least 10.0%, at least 10.5%, or at least 11.0%. The coating suspension can have a solids content of at most 13.0%, at most 12.5%, at most 12.0%, at most 11.5%, at most 11.0%, at most 10.5%, or at most 10.0%.

In certain cases, the coating suspension can have a viscosity of at least 1150 cP at 10% solids content when mechanically stirred via a multi-action stirring blade at 900 rpm to 1200 rpm. The viscosity can decrease under high-shear stirring at 4000 rpm to 6000 rpm.

The present disclosure provides a coating. The coating is the result of applying the coating suspension to an article in accordance with the methods described herein. The coating can include the same or substantially similar components as described elsewhere herein with respect to the coating composition, minus any volatile components that are removed in the coating process, as would be understood by a person having ordinary skill in the art.

The present disclosure provides a coated substrate. The coated substrate is the result of applying the coating suspension to a substrate in accordance with the methods described herein. The coated substrate includes the substrate and the coating, as described elsewhere herein. While the properties of the coating composition are described with respect to the coating of a specific substrate in a specific fashion (as described herein), the composition can be used to coat a wide variety of substrates, including but not limited to, food products.

In certain cases, the substrate can be a nutraceutical, including gummy nutraceuticals, nutraceuticals containing probiotics, and the like, cereal, candy, including gummy candies, lozenges, gum, or the like.

The present disclosure provides a method of making a coating composition and/or suspension.

The method of making the coating composition can include combining and/or milling the various components of the coating composition. In some cases, dry ingredients are mixed first and wet ingredients are added while stirring.

The method of making the coating suspension can include: 1) stirring a desired amount of solvent, optionally stirring at a level sufficient to generate a vortex; 2) adding a desired amount of the coating composition; and 3) mixing until a suspension forms.

The present disclosure provides a method of using a coating composition and/or suspension.

In cases where the coating composition is the starting material, the method of using the coating composition can include preparing a coating suspension having a solids content as described elsewhere herein. The method can then continue with the method described below with respect to the coating suspension.

In cases where the coating suspension is the starting material, the method of using the coating suspension can include applying the coating suspension to a plurality of uncoated substrates. The applying can be in compliance with the parameters outlined in Table 1 below. In some cases, the coating suspension can be stirred above a certain velocity and/or heated above a temperature where pectin "detangles" (i.e., where individual pectin molecules become uncoiled/denatured or disassociated with other pectin molecules and/or non-glycerol sugar alcohol molecules) prior to applying the coating suspension. In these cases, the method includes cooling the coated substrate in order to "rectangle" the pectin (i.e., where individual pectin molecules become recoiled/renatured or reassociated with other pectin molecules and/or non-glycerol sugar alcohol molecules). In some cases, this detangling can be identified by a thinning or reduction in viscosity of the suspension.

TABLE 1

FLEXICOAT ™ COATING PARAMETERS

| Pan Size | 15 in | 24 in | 48 in | 60 in |
|---|---|---|---|---|
| Air Volume cfm | 280 to 320 | 280 to 350 | 1,900 to 2,400 | 3,800 to 4,800 |
| Inlet Temp (° C.) | 35 to 40 | 35 to 40 | 35 to 40 | 35 to 40 |
| Outlet Temp (° C.) | 28 to 35 | 28 to 35 | 28 to 35 | 28 to 35 |
| Pre-Warm Temp (° C.) | 26 to 33 | 26 to 33 | 26 to 33 | 26 to 33 |
| Spray Rate (g/min) | 9 | 20 | 80 to 100 | 175 to 200 |
| Atomizing Air (psi) | 21 to 23 | 28 to 35 | 50 to 60 | 50 to 70 |
| Pattern Air (psi) | 25 | 35 | 50 to 60 | 50 to 75 |
| Number of Guns | 1 | 2 | 3 to 4 | 4 to 6 |
| Pan Speed (rpm) | 15 to 20 | 12 to 18 | 5 to 15 | 4 to 8 |
| Charge wt (kg) | 1 to 3 | 15 to 20 | 120 to 200 | 250 to 350 |
| Solids content (% w/w) | 25 to 30% | 25 to 30% | 25 to 30% | 25 to 30% |

Substrates that are coated with the composition herein using the coating methods herein can have certain advantageous properties. These improved properties are described in terms of exposure to predetermined conditions for a predetermined length of time. The predetermined conditions can be a predetermined temperature and/or a predetermined relative humidity. In certain cases, the predetermined temperature can be 25° C., 30° C., 35° C., 40° C., 45° C., or 50° C. In certain cases, the predetermined relative humidity can be 50%, 55%, 60%, 65%, 70%, 75%, 80%, or 85%. The predetermined length of time can be 6 hours, 12 hours, 24 hours or 1 day, 2 days, 3 days, 5 days, 7 days or 1 week, 10 days, 14 days or 2 weeks, 17 days, 25 days, 28 days or 4 weeks, 56 days or 8 weeks, 84 days or 16 weeks, or 168 days or 32 weeks.

Some specific conditions were utilized in experiments described herein, but these conditions are only exemplary and are not intended to be limiting. As used herein, "H2" refers to a predetermined temperature of 25° C. and a predetermined relative humidity of 60%. As used herein, "H4" refers to a predetermined temperature of 40° C. and a predetermined relative humidity of 75%.

In some cases, the coating composition described herein can provide improved structural integrity to substrates to which it is applied. One method for measuring this improved structural integrity involves applying the coating composition to a substrate that, under predetermined conditions, undergoes a reduction in loose-packed volume without having the coating applied. To test this structural integrity, a predetermined amount of the substrate can be loosely packed into a container (for example, adding a predetermined amount of the substrate to a beaker or ajar, lightly shaking the beaker or the jar to ensure that there is not a blockage that is preventing loose-packed settling) and exposed to predetermined conditions. It should be apparent to that in order to provide improved structural integrity, the substrate itself must suffer from some lack of structural integrity without the coating. Thus, in order for this test to be relevant, the uncoated substrate must fail the test. In certain cases, this test can be performed on off-the-shelf gummy bears, such as Great Value Gummy Bears Chewy Candy, Black Forest Gummy Bears Candy, or Haribo® Gold-Bears, all available commercially from Walmart, Bentonville, AR.

In some cases, the coating composition described herein can provide improved resistance to sticking for substrates to which it is applied, in cases where the substrates that are not coated with the coating composition are susceptible to sticking. To test the improved resistance to sticking, a predetermined amount of the substrate can be loosely packed into a container as described above and exposed to predetermined conditions. After exposure to the predetermined conditions, the predetermined amount of the substrate are removed from the container by dumping. The removed substrates can be fanned out into a single layer by applying light pressure by hand. If the substrates are so agglomerated that a single layer cannot be formed, then the test is fails (i.e., a determination of sticking is made). If the single layer is formed, then the test is passed if at least 50%, at least 60%, at least 70%, at least 80%, or at least 90% of individual substrates can be lifted from the surface on which the single layer is formed without co-lifting a different substrate to which the individual substrate is attached. It should be apparent that in order to provide improved resistance to sticking, the substrate itself must suffer from some sticking without the coating. Thus, in order for this test to be relevant, the uncoated substrate must fail the test.

In some cases, the coating composition described herein can provide substantially unchanged optical properties for the substrate to which it is applied. In other words, the coating composition can provide a coating that is substantially transparent and/or that is substantially unchanging of a color value of the underlying substrate. This substantial transparency and/or unchanging color value can be resilient to exposure to the predetermined conditions for the predetermined length of time.

In some cases, the coating composition described herein can reduce or prevent the leeching of certain components of the substrate or liquid filled gummies to which it is applied. As one non-limiting example, gummy bears that are not coated can leech various oils under exposure to predetermined conditions, such as H4 conditions, but coating the gummy bears with the coating composition described herein can reduce or eliminate the leeching of these oils. One test for this property is to weigh a substrate prior to exposure and after exposure. If the weight is reduced, the one or more components of the substrate has left the substrate. Another test for this property is to remove the substrates from the container in which they were stored under the predetermined conditions and analyze the contents of the container (using standard analytical techniques, such as chromatography and/or mass spectrometry) to determine if the substrates "left behind" any of their components in the container. In certain cases, the coating composition described herein can reduce the leeching of components of the substrate by at least 10%, at least 20%, at least 25%, at least 30%, at least 40%, at least 50%, at least 60%, at least 70%, at least 75%, at least 80%, at least 85%, at least 90%, or at least 95%.

In some cases, the coating composition described herein can improve resistance to melting and/or deshaping under elevated temperatures. One test to determine this is placing an uncoated substrate, such as a gelatin gummy, and a coated substrate in an oven at a starting temperature, such as 30° C., for one hour intervals and increasing the temperature by 5° C. every hour. Uncoated gelatin gummies begin softening at 40° C. and completely melt/deform at 45° C. Coated gummies retain their original shape integrity to temperatures of at least 55° C. or 60° C.

EXAMPLES

Example 1

Formulation 1

| Ingredient | Amount (percent by weight) |
| --- | --- |
| Pectin Type DSS | 40.000% |
| Flavorant (mixed berry) | 10.000% |
| Stevia | 1.000% |
| Sorbitol | 20.000% |
| Glycerin | 4.000% |
| MCT | 10.000% |
| HPC SSL | 5.000% |
| Carnauba Wax | 10.000% |

Formulation 1 was prepared by adding the dry ingredients together and mixing, followed by adding the glycerin and mixing, thus allowing the glycerin to absorb into the powders. After that, the MCT was charged and momentarily mixed. 20 g of the resulting blend was added to 180 g of stirring water at 700 rpm. The volume of the solution was noted, the solution was allowed to stir overnight, and water was then added to bring the solution back to the original volume.

One 300 g batch and one 200 g batch of Walmart Brand gummy bears were coated in separate pans using the processing conditions/results described below in Table 2. Note: the results for the 300 g batch are shown, but the parameters for the 200 g batch were the same, with the results being different based on the different starting mass.

TABLE 2

| Processing Conditions (Coating) and RESULTS | | | |
| --- | --- | --- | --- |
| Equipment: | Vector Pan: 0.5 L | # of Guns: 1 | |
| Nozzle Size Info.: | Tip: (w44019) #10, Cap: (w44183) #27, Ring: (Schilick e45738) | | |
| Pan Speed Target (rpm) | 2→30 | Pump Speed (rpm) 5 | |
| Inlet Target (° C.) | 30→35 | | Record |
| Coater Airflow (cfm) | 57 | Actual Solution Amount Used (g) | 30.0 |
| Atom. (psi) Target | na | Actual Coated Weight: (g) | 303 |
| Pattern Air Flow (psi) | na | Actual Average Spray rate (g/min) | 2.0 |
| Exhaust (° C.) Target | 25-32 | Total Spray Time (min.) | 15.1 |
| Theo. Solution Ant (g) | 30 | Actual Weight gain (%) | 1.00% |

150 g of coated 1% weight gain gummies were placed into three sealed glass jars and placed in H4, H2, and RT conditions. Three batches of 150 g of uncoated gummies were placed into glass jars and sealed as controls under the same three sets of conditions. The loose-packed volume of each of these batches of gummies was ~200 mL.

After 12 hours of H4 conditions, the uncoated gummies were melted together at the bottom of the jar, while the coated gummies had retained much of their original shape, albeit with slight wrinkling on the surface of the gummies. The coated batch largely retained its loose-packed volume of ~200 mL and the uncoated batch had its loose-packed volume reduced to less than 150 mL. Oils were secreted from the uncoated batch and the oils were visible on the walls of the container. The coated batch did not have these visible oils.

After 48 hours of H4 conditions, the above-referenced effects were even more dramatic. The uncoated gummies were even more melted together. Again, the coated batch largely retained its loose-packed volume of ~200 mL, whereas the uncoated batch had its loose-packed volume reduced to ~100 mL. The oils became even more prevalent in the uncoated batch.

After 12 and 48 hours of H2 and RT conditions, the coated and uncoated batches were visible quite similar, except the uncoated batch had visible oil on the walls of the container.

Example 2

Formulation 2

| Ingredient | Amount (percent by weight) |
| --- | --- |
| Pectin Type DSS | 3.00% |
| Sorbitol | 1.50% |
| Spirulina Color Suspension | 8.33% |
| Deionized Water | 87.17% |

Formulation 3

| Ingredient | Amount (percent by weight) |
| --- | --- |
| Pectin Type DSS | 4.00% |
| Sorbitol | 2.00% |
| Natural Blue Color Suspension | 11.0% |
| Glycerin | 0.40% |
| Deionized Water | 82.60% |

Formulation 2 was formed by first preparing an aqueous solution of pectin and sorbitol by dissolving 6 g of pectin and 3 g of sorbitol in 174 mL of water under high shear. The resultant mixture sat overnight to expel trapped air and the resulting viscosity was lowered. 16.67 g of Spirulina Color Suspension was added under low shear. Formulation 3 was formed by the same procedure as Formulation 2, substituting 11.0% of Natural Blue Suspension and adding 0.40% of glycerin and adjusting proportions to meet the requirements Formulation 3.

The modified Flexicoat solutions were added to the Compact DeVilbiss HVLP Spraygun and sprayed onto 59.16 g dry cereal in a rotating pan with warm air drying. 53.09 g of Formulation 2 was applied with a negligible amount remaining on the pan after drying. Cereal was then coated with 50 g of 80 Brix sucrose syrup and tumbled with warm air to dry.

The final product was 35% sugar by mass. The same process was repeated for Formulation 3.

Color stability in milk was tested by placing 5 g of coated cereal in 20 g milk for 5 minutes and measuring reflectance (25 mm) of the colored milk versus unadulterated milk.

The formulations facilitated even coverage of pieces and reduced clumping of pieces due to wetness. Color bleed for formulation 2 was comparable to commercially-available colored cereals.

We claim:

1. A coated gummy dosage form comprising a gummy dosage form substrate having a coating thereon, the coating formed from a coating composition comprising:
   a pectin in an amount by weight of at least 30.0% and at most 50.0%; and
   a non-glycerol sugar alcohol in an amount by weight of at least 10.0% and at most 40.0%,
wherein the coated gummy dosage form retains a greater loose packed volume when compared with an uncoated gummy dosage form comprising the gummy dosage form substrate without the coating following exposure of the coated gummy dosage form and the uncoated gummy dosage form to a temperature of 40° C. and a relative humidity of 75% for a length of time of 12 hours.

2. The coated gummy dosage form of claim 1, wherein the pectin has a degree of methyl esterification of greater than 50.

3. The coated gummy dosage form of claim 1, wherein the pectin has a molecular weight of at least 60,000 grams per mole.

4. The coated gummy dosage form of claim 1, wherein the non-glycerol sugar alcohol is sorbitol.

5. The coated gummy dosage form of claim 1, wherein the coating composition is substantially free of divalent cations.

6. The coated gummy dosage form of claim 1, wherein the coating composition is substantially free of calcium or magnesium.

7. The coated gummy dosage form of claim 1, the coating composition further comprising glycerin in an amount by weight of at least 0.01% and at most 20.0%.

8. The coated gummy dosage form of claim 1, the coating composition further comprising an oil-based plasticizer in an amount by weight of at least 0.01% and at most 15.0%.

9. The coated gummy dosage form of claim 1, the coating composition further comprising a film forming agent in an amount by weight of at least 0.01% and at most 15.0%.

10. The coated gummy dosage form of claim 1, the coating composition further comprising an opacifying agent in an amount by weight of at least 0.01% and at most 20.0%.

11. The coated gummy dosage form of claim 1, the coating composition further comprising a wax in an amount by weight of at least 0.01% and at most 5.0%.

12. The coated gummy dosage form of claim 1, the coating composition further comprising a non-sugar-alcohol sweetening agent in an amount by weight of at least 0.01% and at most 10.0%.

13. The coated gummy dosage form of claim 1, the coating composition further comprising an adjuvant.

14. The coated gummy dosage form of claim 1, the coating composition further comprising a spray dried flavorant, a dried crystal flavorant, a granule flavorant, or a combination thereof in an amount by weight of at least 3.0% and at most 15.0%.

15. The coated gummy dosage form of claim 1, the coating composition further comprising a liquid flavorant in an amount by weight of at least 0.1% and at most 9.0%.

16. The coated gummy dosage form of claim 1, the coating composition further comprising a spray dried sensate, a dried crystal sensate, a granule sensate, or a combination thereof in an amount by weight of at least 3.0% and at most 15.0%.

17. The coated gummy dosage form of claim 16, wherein the spray dried sensate, the dried crystal sensate, the granule sensate, or a combination thereof provides a hot sensation, a cool sensation, a tingling sensation, or a combination thereof.

18. The coated gummy dosage form of claim 1, the coating composition further comprising a liquid sensate in an amount by weight of at least 0.1% and at most 9.0%.

19. A method of improving structural integrity in a gummy dosage form by using a coating suspension, the method comprising applying the coating suspension to a gummy dosage form substrate, the coating suspension comprising a coating composition and a solvent, the coating composition comprising a pectin in an amount by weight of at least 30.0% and at most 50.0% and a non-glycerol sugar alcohol in an amount by weight of at least 10.0% and at most 40.0%, wherein the resulting coated gummy dosage from produced by the method retains a greater loose packed volume when compared with an uncoated gummy dosage form comprising the gummy dosage form substrate without application of the coating suspension following exposure of the coated gummy dosage form and the uncoated gummy dosage form to a temperature of 40° C. and a relative humidity of 75% for a length of time of 12 hours.

* * * * *